US011759473B2

(12) United States Patent
Dellinger

(10) Patent No.: US 11,759,473 B2
(45) Date of Patent: *Sep. 19, 2023

(54) TOPICAL COMPOSITIONS INCORPORATING SILICA FIBERS

(71) Applicant: American Nano, LLC., Clemmons, NC (US)

(72) Inventor: Mitch Dellinger, Clemmons, NC (US)

(73) Assignee: American Nano, LLC, Clemmons, NC (US)

( * ) Notice: Subject to any disclaimer, the term of this patent is extended or adjusted under 35 U.S.C. 154(b) by 133 days.

This patent is subject to a terminal disclaimer.

(21) Appl. No.: 16/367,313

(22) Filed: Mar. 28, 2019

(65) Prior Publication Data

US 2019/0269709 A1  Sep. 5, 2019

Related U.S. Application Data

(63) Continuation-in-part of application No. 16/131,531, filed on Sep. 14, 2018, now abandoned, which is a
(Continued)

(51) Int. Cl.
*A61P 17/02* (2006.01)
*A61K 31/675* (2006.01)
(Continued)

(52) U.S. Cl.
CPC .......... *A61K 31/695* (2013.01); *A61K 9/0017* (2013.01); *A61K 31/167* (2013.01);
(Continued)

(58) Field of Classification Search
CPC .... A01N 25/10; A01N 37/44; A01N 2300/00; A01N 25/34; A01N 31/0801;
(Continued)

(56) References Cited

U.S. PATENT DOCUMENTS 4,563,184 A   1/1986  Korol
4,786,017 A   11/1988 Wegerhoff et al.
(Continued)

FOREIGN PATENT DOCUMENTS

CN   102652903       9/2012
CN   105133298 A    12/2015
(Continued)

OTHER PUBLICATIONS

Yetman. https://www.healthline.com/health/how-to-prevent-scarring. Published: May 17, 2020.*
(Continued)

*Primary Examiner* — Nicole P Babson
*Assistant Examiner* — Lori K Mattison
(74) *Attorney, Agent, or Firm* — Morgan, Lewis & Bockius LLP

(57) ABSTRACT

Embodiments of the invention include topical compositions comprising silica fiber powder or dust and a topical carrier, for treatment of skin tissue. The silica fiber powder or dust may be generated from silica fiber mats that may be formed via electrospinning of a sol gel produced with a silicon alkoxide reagent, such as tetraethyl ortho silicate, alcohol solvent, and an acid catalyst.

21 Claims, 8 Drawing Sheets

Related U.S. Application Data continuation-in-part of application No. 15/934,599, filed on Mar. 23, 2018, now Pat. No. 10,111,783.

(60) Provisional application No. 62/729,085, filed on Sep. 10, 2018, provisional application No. 62/651,386, filed on Apr. 2, 2018, provisional application No. 62/643,946, filed on Mar. 16, 2018, provisional application No. 62/710,305, filed on Feb. 16, 2018.

(51) Int. Cl.
| | |
|---|---|
| A61K 9/00 | (2006.01) |
| A61K 31/695 | (2006.01) |
| A61K 38/12 | (2006.01) |
| A61K 33/14 | (2006.01) |
| A61K 31/352 | (2006.01) |
| A61K 31/167 | (2006.01) |
| A61K 31/573 | (2006.01) |
| A61P 17/10 | (2006.01) |
| A61K 45/06 | (2006.01) |

(52) U.S. Cl.
CPC .......... *A61K 31/352* (2013.01); *A61K 31/573* (2013.01); *A61K 33/14* (2013.01); *A61K 38/12* (2013.01); *A61P 17/02* (2018.01); *A61P 17/10* (2018.01); *A61K 45/06* (2013.01)

(58) Field of Classification Search
CPC ........ A01N 31/14; A01N 33/12; A01N 37/18; A01N 37/26; A01N 41/10; A01N 43/40; A01N 43/653; A01N 59/16; A01N 25/18; A61P 31/04; A61P 17/02; A61P 17/16; A61P 31/00; A61P 31/10; A61P 7/04; A61K 31/7048; A61K 31/722; A61K 33/22; A61K 31/14; A61K 31/155; A61K 31/785; A61K 33/00; A61K 33/08; A61K 33/34; A61K 33/38; A61K 9/501; A61K 9/7007

See application file for complete search history.

(56) References Cited

U.S. PATENT DOCUMENTS

| | | | |
|---|---|---|---|
| 5,688,955 A * | 11/1997 | Kruse | C07D 213/56 546/276.4 |
| 6,342,237 B1 | 1/2002 | Bara | |
| 7,563,461 B2 | 7/2009 | Modak et al. | |
| 8,088,965 B2 | 1/2012 | Thierauf | |
| 8,173,154 B2 | 5/2012 | Jung et al. | |
| 8,512,741 B2 | 8/2013 | Tan | |
| 8,535,710 B2 | 9/2013 | Jung et al. | |
| 8,647,557 B2 | 2/2014 | Yeo | |
| 8,747,927 B2 | 6/2014 | Florence et al. | |
| 8,821,919 B2 | 9/2014 | Jung | |
| 9,486,554 B2 | 11/2016 | Jung et al. | |
| 9,498,459 B2 | 11/2016 | Pomrink et al. | |
| 9,554,463 B2 | 1/2017 | Sethumadhavan | |
| 10,624,982 B2 | 4/2020 | Jung et al. | |
| 11,286,097 B2 | 3/2022 | Jung | |
| 2002/0182238 A1 | 12/2002 | Creton | |
| 2002/0197288 A1 | 12/2002 | Chevalier | |
| 2006/0034816 A1 | 2/2006 | Davis et al. | |
| 2008/0187996 A1 | 8/2008 | Baca et al. | |
| 2008/0220026 A1 | 9/2008 | Maitra et al. | |
| 2009/0186013 A1 | 7/2009 | Stucky et al. | |
| 2010/0063152 A1 | 3/2010 | Bhushan et al. | |
| 2011/0183419 A1 | 7/2011 | Glaubitt | |
| 2012/0244292 A1 | 9/2012 | Lee | |
| 2013/0115186 A1 | 5/2013 | Baecker | |
| 2013/0115187 A1* | 5/2013 | Baecker | A61P 19/10 424/78.37 |
| 2014/0037958 A1 | 2/2014 | Gerber | |
| 2015/0225278 A1 | 8/2015 | Jung | |
| 2015/0366908 A1 | 12/2015 | Pomrink et al. | |
| 2016/0271294 A1* | 9/2016 | Gerashchenko | A61P 13/02 |
| 2018/0043055 A1 | 2/2018 | Bjork et al. | |

FOREIGN PATENT DOCUMENTS

| | | |
|---|---|---|
| DE | 19609551 | 7/1997 |
| JP | 2002-128639 A | 5/2002 |
| WO | 2006069567 | 7/2006 |
| WO | 2008086970 | 7/2008 |
| WO | WO 2008/111609 A1 | 9/2008 |
| WO | 2017186201 | 11/2017 |

OTHER PUBLICATIONS

Silica Topically—Other Advantages. https://web.archive.org/web/20161130022936/https://silicea.com.au/what-is-silicea/silicea-gel-topically-other-advantages/. Published: Nov. 30, 2016.*
Contractures, https://stanfordhealthcare.org/medical-treatments/s/scar-revision-surgery/procedures/contractures.html#:~:text=Contractures%20are%20an%20abnormal%20occurrence,a%20tight%20area%20of%20skin. Published 2022.*
Hyland. Aust Prescr 2015;38:124-7.*
Brissett. Facial PlastSurg. Nov. 2001;17(4):263-72.*
Bacitracin, https://medlineplus.gov/druginfo/meds/a614052.html. Published: Mar. 15, 2017.*
Quignard. Colloids and Surfaces B: Biointerfaces 155 (2017) 530-537.*
Wound Care. https://uwmsktc.washington.edu/sites/uwmsktc/files/files/Burn_wound_3-16.pdf. Published 2011.*
International Search Report and Written Opinions for International Application No. PCT/US2019/017921, dated Jun. 11, 2019, 10 pages.
International Search Report and Written Opinions for International Application No. PCT/US2019/024456, dated Jul. 11, 2019, 11 pages.
Choi, et al., "Silica Nanofibers From Electrospinning/Sol-Gel Process," Journal of Materials Science Letters 22, 2003, 891-893.
Geltmeyer, et al., "The Influence of Tetraethoxysilane Sol Preparation on the Electrospinning of Silica Nanofibers," J Sol-Gel Sci Technol (2016) 77:453-462.
Milea et al., The Influence of Parameters in Silica Sol-Gel Process, Bulletin of the Transilvania University of Brașov Series I: Engineering Sciences • vol. 4 (53) No. 1-2011.
Sakka et al., "The Sol-Gel Transition in the Hydrolysis of Metal Alkoxides in Relation to the Formation of Glass Fibers and Films," Journal of Non-Crystalhne Solids 48 (1982) 31-46.
International Search Report and Written Opinions for International Application No. PCT/US2019/017921, 12 pages.
International Search Report and Written Opinions for International Application No. PCT/US2019/024456, dated Jul. 11, 2019, 13 pages.
Vera Grotheer, et al., "The performance of an orthosilicic acid-releasing silica gel fiber fleece in wound healing," Biomaterials, vol. 34 (2013), pp. 7314-7327.
A. Freyer, et al., "Electrospun Silica Nanofiber Mats: Effects of Sol Viscosity and Application to Thin Layer Chromatography," 2014 American Chemical Society, pp. 139-150.
Kenji Iimura, et al., "Preparation of silica fibers and non-woven cloth by electrospinning," Advanced Powder Technology, vol. 21 (2010), pp. 64-68.
Kursawe, et al., "Biodegradable Silica Fibers from Sols," Journal of Sol-Gel Science and Technology; New York vol. 13, Iss. 1-3, (Jan. 1998): 267-271.
Veverkova, et al., "Modified Silica Nanofibers with Antibacterial Activity," Journal of Nanomaterials, vol. 2016, Article ID 2837197, 6 pages (2016).
Wei, et al., "Preparation of Silica Nano-fiber by Electrostatic Spinning," Journal of Fujian Normal University (Natural Science Edition), vol. 30, No. 1, pp. 85-90 (Jan. 2014).

* cited by examiner

TOPICAL COMPOSITIONS INCORPORATING SILICA FIBERS

RELATED APPLICATIONS

This application is a continuation-in-part of U.S. patent application Ser. No. 16/131,531, filed Sep. 14, 2018, which is a continuation-in-part of U.S. patent application Ser. No. 15/934,599, filed Mar. 23, 2018, which claims the benefit of and priority to U.S. Provisional Patent Application No. 62/710,305, filed Feb. 16, 2018, and U.S. Provisional Patent Application No. 62/643,946, filed Mar. 16, 2018, the entire disclosure of each of which is hereby incorporated herein by reference. This application claims the benefit of and priority to U.S. Provisional Patent Application No. 62/729,085, filed Sep. 10, 2018, and U.S. Provisional Patent Application No. 62/651,386, filed Apr. 2, 2018, the entire disclosure of each of which is hereby incorporated herein by reference.

TECHNICAL FIELD

In various embodiments, the present invention relates to topical compositions incorporating silica fibers as an additive.

BACKGROUND

Collagen is a protein that provides the matrix that sustains the body's structures. It provides integrity, firmness and elasticity to tissues. Loss of collagen results in the wrinkles, lines, and loss of smoothness associated with aging skin. Since collagen is not significantly absorbed through the skin, nutritional supplements are sometimes used to boost collagen levels, even though collagen is also poorly absorbed as a dietary supplement.

Topical products that improve the integrity of skin, including aging or damaged skin, are of great need.

SUMMARY

In accordance with various embodiments, the present invention provides topical compositions that comprise a silica fiber powder or dust (e.g., a collection of fibrous fragments) and a topical carrier. Embodiments of the invention further provide methods for treating aging or damaged skin of a subject. In various embodiments, the methods involve application of the compositions to improve skin healing, to prevent or reduce scarring, reduce signs of aging, and/or to reduce pain and/or irritation associated with damaged or diseased skin.

In various embodiments, the topical composition when applied to skin allows silica fiber dust to be deposited in macroscopic or microscopic breaks in skin. The fiber dust or flakes may act as a collagen mimetic that is not substantially biodegradable, and which may promote cell infiltration and/or collagen deposition, and in some embodiments reduces local production of pain and inflammatory mediators. The topical carrier may be in the form of a lotion, ointment, paste, cream, foam, balm, soap, shampoo, or gel, and may include other active agents.

In accordance with various embodiments, the fiber composition is prepared by electrospinning a sol-gel into a silica fiber composition, followed by processing the fiber into a fine powder or dust, and incorporating the powder or dust with the topical carrier. In some embodiments, the silica fiber composition is electrospun from a gelatinous material into a lightweight fiber mat. For example, the composition may be prepared by electrospinning a sol-gel, which may be prepared with a silicon alkoxide reagent, such as tetraethyl ortho silicate (TEOS), alcohol solvent, and an acid catalyst. In various embodiments, the sol-gel is produced via ripening of sol under controlled environmental conditions, and/or the properties of the sol or sol-gel during the ripening process are monitored, in order to identify various processing windows during which the electrospinning of the sol-gel may be successfully performed. As known in the art, a "sol" is a colloidal solution that gradually evolves towards the formation of a "gel," i.e., a diphasic system containing both a liquid phase and solid phase. Herein, the term "sol-gel" is used to refer to the gel produced from the sol-gel process that may be electrospun into fibers or a fibrous mat.

Known processes for electrospinning silica fibers do not yield a fiber composition with sufficient flexibility and texture suitable or ideal for many applications. By slowly ripening the sol-gel under controlled environmental conditions, and/or monitoring the sol-gel during the ripening process, the relatively short window to successfully electrospin the sol-gel may be identified and increased in duration. In accordance with embodiments of the invention, the composition is non-rigid and has a soft texture similar to that of cotton. In some embodiments, the sol-gel is electrospun after a ripening process of at least 2 days, or at least 3 days (e.g., from 2 to 7 days), under the controlled environmental conditions. The weight of the sol-gel and/or emission of ethylene vapors can be used as an indicator of when the sol-gel is at or near the ideal time to electrospin.

In various embodiments, the controlled environment for ripening (or "transitioning") the sol may involve controlled conditions in terms of humidity, temperature, and optionally barometric pressure. For example, the humidity may be controlled within the range of about 30% to about 90% or from about 40% to about 80%, and the temperature may be controlled within the range of from about 50° F. to about 90° F. By controlling the environmental conditions during ripening, the gel may be electrospun during the time when spinning is optimal, which can occur in a very small window of only several minutes if the ripening process is accelerated by direct heat. When ripening the sol at a constant humidity in the range of about 50% to 70% or 80% and a temperature of about 60 to 80° F., the sol will ripen (gelatinize) in a few days, and the window for successful electrospinning may be expanded to at least several hours, and in some embodiments several days. The sol may therefore be ripened in an enclosure which may include one or more environmental monitors, such as a temperature reading device and/or a humidity reading device. Further, gases produced or released by the sol during the ripening process and/or relative weight of the sol may be monitored to determine a suitable or optimal time for electrospinning.

Once the sol is adequately ripened into a sol-gel, it is electrospun to form a mat of entangled silica fibers. Once electrospun, the silica fibers may have a variable diameter, such as in the range of from about 50 nm to 5 In some embodiments, the fibers are predominately in the range of about 100 nm to about 2 or predominately in the range of about 200 to about 1000 nm. After the silica-fiber mat is successfully formed, it is, in various embodiments, divided into small fibrous fragments that are utilized as an additive in any of a variety of different topical compositions. For example, the electrospun mat may be "fragmented," i.e., fractured, cut, ground, milled, or otherwise divided into small fragments that maintain a fibrous structure. As used herein, the term "fibrous fragments" (or "fibrous-mat fragments," or simply "fragments") refers to small particles, parts, or flakes of a fibrous mat having an average dimension larger (e.g., 5×, 10×, or even 100×) than the width of at least some of the fibers of the mat. In various embodiments, the average size of a fibrous fragment is in the range of approximately 20 μm to approximately 200 μm. Fibrous fragments may thus resemble microscopic-scale versions of the electrospun mat itself, e.g., intertwined collections of silica fibers, and thus typically are porous and have low densities. Thus, fibrous fragments may be contrasted with other types of micro-scale particles, such as the substantially spherical particles used in colloidal silica, which are each unitary, individual units or grains, rather than small collections of fibers. Various portions of a fibrous fragment (e.g., the edges) may have sharp and/or broken edges resulting from the fracturing process utilized to form the fragments from the electrospun mat. As utilized herein, the term "fiber dust" includes collections of particles generated via the fragmentation of electrospun fiber mats and/or fibers, and may include fibrous fragments and/or other powder particles resulting from such fragmentation.

Embodiments of the present invention may employ silica fibers, fragments thereof, and/or compositions incorporating such fibers or fragments, and/or methods for fabricating such fibers or fragments detailed in U.S. patent application Ser. No. 15/934,599, filed on Mar. 23, 2018 (issued as U.S. Pat. No. 10,111,783), and U.S. patent application Ser. No. 16/131,531, filed on Sep. 14, 2018, the entire disclosure of each of which is incorporated by reference herein.

The fiber dust or fibrous fragments are incorporated with a topical carrier. The topical composition may be a skin care composition or a cosmetic composition. In some embodiments, the fiber dust or fragments are distributed in a carrier system such as water or any aqueous solution containing organic or inorganic materials. The compositions may contain one or more ingredients to modify or enhance their texture, appearance, scent performance or stability. Illustrative additives to the compositions include: oily components, fatty components, ointment bases, hydrophilic solvents, lipophilic solvents, emollients, water, buffering agents, pH-adjusting agents, preservatives, humectants, chelating agents, antioxidants, stabilizers, emulsifying agents, suspending agents, gel-forming agents, perfumes and fragrances, skin protective agents, and antiseptics.

In some embodiments, the composition further comprises one or more anti-inflammatory agents such as steroidal anti-inflammatory agents or non-steroidal anti-inflammatory agents (NSAIDs). In some embodiments, the composition further comprises one or more antimicrobial agents. In some embodiments, the composition further comprises one or more pain reducing agents.

In various embodiments, the invention provides a method for treating skin tissue in a subject, which comprises applying the topical composition to skin tissue. The composition can be used routinely or periodically. In some embodiments, the composition is applied at least about daily. In various embodiments, the method improves healing of the skin tissue and/or prevents or reduces tissue scarring, looseness of skin, age spots, pain, and/or irritation.

Application of the composition can provide for improved or accelerated healing of damaged skin. For example, when the topical composition is applied to skin that has cracks, small scrapes, blemishes, etc., the scaffolding is left behind in the small "wound" for cells to grow into. This speeds up the healing process and helps to reduce scarring. In some embodiments, the composition is applied to cracked skin, which can improve tolerance of the skin to the environment, such as sun, wind, and cold.

In some embodiments, the composition is applied to a skin lesion, superficial wound or infection, acne, burn, ulcer, cut, scrape, rash, blister, allergic reaction, hives, or insect or spider bites or stings. Exemplary conditions include aging skin, dry skin, eczema, pruritus, sun burn, reaction to poison ivy or poison oak, post-surgery wound, skin graft, mosquito bites, and genetic diseases that impact skin integrity (such as but not limited to epidermolysis bullosa and ichthyosis). In some embodiments, the composition is applied to diseased skin, which can be a manifestation of a proliferative disorder (e.g., carcinoma or pre-carcinoma, such as a melanoma lesion, or psoriasis), or in some embodiments an autoimmune or inflammatory disorder, such as rosacea, acne, cutaneous manifestation of lupus, or dermatitis herpetiformis. In some embodiments, the composition is applied to a microbial infection of the skin. In some embodiments, the composition is applied to skin affected by shingles, providing, for example, relief from associated pain. Other conditions that may benefit from the pain reducing properties of the invention include neuropathy, joint pain, and gout.

In an aspect, embodiments of the invention feature a topical composition comprising, consisting essentially of, or consisting of a silica fiber powder or dust, and a topical carrier.

Embodiments of the invention may include one or more of the following in any of a variety of combinations. The topical carrier may be a lotion, ointment, balm, paste, cream, foam, soap, shampoo, bath salt, and/or gel. The composition may further include one or more pharmaceutical or antimicrobial agents. The composition may further include an antibiotic and/or antiseptic. The composition may further include an anti-inflammatory agent, immunosuppressant, and/or pain-reducing agent. The composition may further include an anti-fibrotic and/or anti-scarring agent.

The composition may be prepared by electrospinning a sol-gel into a silica fiber composition, processing the silica fiber composition into powder or dust, and incorporating the powder or dust with the topical carrier. The sol-gel may be prepared with tetraethyl orthosilicate (TEOS). Prior to electrospinning the sol-gel, the sol-gel may be produced from an initial sol comprising, consisting essentially of, or consisting of 70% to 90% TEOS by weight, 8% to 25% ethanol by weight, an acid catalyst, and water. The initial sol may comprise, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may comprise, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may comprise, consist essentially of, or consist of 70% to 90% TEOS by weight, 8% to 25% ethanol by weight, an acid catalyst, and water. The initial sol may comprise, consist essentially of, or consist of 70% to 90% TEOS by weight, 8% to 25% ethanol by weight, 1% to 10% water by weight, and the acid catalyst. The initial sol may comprise, consist essentially of, or consist of 75% to 85% by weight TEOS, 12% to 20% by weight ethanol, and about 2% to 5% by weight water. The initial sol may comprise, consist essentially of, or consist of about 80% by weight TEOS, about 17% by weight ethanol, and about 3% by weight water. The acid catalyst may comprise, consist essentially of, or consist of HCl. The initial sol may contain less than about 0.1% of the acid catalyst by weight. The initial sol may contain from 0.02% to 0.08% of the acid catalyst by weight. The initial sol may contain one or more reagents that alter one or more properties of the initial sol, the sol-gel, and/or the silica fibers.

Producing the sol-gel may include transitioning the initial sol for at least 2 days under conditions where humidity is within the range of about 40% to about 80%, and the temperature is within the range of 50° F. to 90° F. The initial sol may be allowed to transition for at least 3 days, at least 4 days, at least 5 days, at least 6 days, or at least 7 days. The initial sol may be allowed to transition for 2 days to 10 days, and for 2 days to 7 days in some embodiments. The sol-gel may be electrospun when the weight is at from 20% to 40% of the starting weight of the initial sol or sol-gel before ripening (transitioning). The sol-gel may be electrospun when the production of ethylene vapor is 10% to 20% relative to the peak production of ethylene vapors during ripening (transitioning) of the initial sol or sol-gel before ripening. The sol-gel may be electrospun when the production of ethylene vapor therefrom is 10% to 40% relative to the initial sol or sol-gel before ripening (transitioning). The powder or dust may comprise, consist essentially of, or consist of particles and/or fibrous fragments that may have an average size (e.g., average diameter, length, width, or other dimension) ranging from approximately 20 μm to approximately 200 μm. The fibers may have a variable diameter of from about 50 nm to about 5 μm. The fibers may have a variable diameter of from about 200 nm to about 1000 nm. The silica fiber powder or dust may consist essentially of or consist of $SiO_2$.

In another aspect, embodiments of the invention feature a method for treating skin tissue in a subject. The method may comprise, consist essentially of, or consist of applying a topical composition to said skin tissue. The topical composition comprises, consists essentially of, or consists of a silica fiber powder or dust, and a topical carrier. The topical composition may comprise, consist essentially of, or consist of any topical composition described herein.

Embodiments of the invention may include one or more of the following in any of a variety of combinations. The method may improve healing of the skin tissue and/or prevent or reduce tissue scarring, pain, and/or irritation. The subject may be a mammal. The subject may be a veterinary patient, such as a dog, cat, or horse. The subject may be a human patient. The composition may be applied to a skin lesion, scar, superficial wound or infection, burn, cut, scrape, rash, blister, bug bite, poison ivy or poison oak, and/or hives. The subject may have a genetic disease of the skin, e.g., epidermolysis bullosa or ichthyosis. The subject may have a first, second, or third degree burn, or combination thereof. The composition may be applied to a sun burn. The composition may be applied to a melanoma lesion. The composition may be applied to aging skin, age spots, dry skin, cracked skin, and/or scar tissue. The composition may be applied to skin affected by eczema and/or atopic dermatitis. The composition may be applied to skin affected by psoriasis. The composition may be applied to skin affected by acne and/or rosacea. The composition may be applied to a post-surgery wound and/or sutures (e.g., sutures utilized to at least partially close a wound). The composition may be applied to skin affected by pruritus. The composition may be applied to skin affected by shingles and/or lupus. The subject may be affected by neuropathy, joint pain, and/or gout. The composition may be applied to skin impacted by dermatitis herpetiformis and/or dermatomyositis. The composition may be applied to skin showing signs of microbial infection and/or skin infected by one or more microbes, such as a virus, bacteria, or fungus. The microbial infection may be HPV, herpes simplex virus, varicella-zoster virus, fungal infection, and/or *staphylococcus* infection. The composition may be applied as a bath including the silica fiber powder or dust (e.g., the topical carrier may include, consist essentially of, or consist of water and/or another bathing fluid).

These and other objects, along with advantages and features of the present invention herein disclosed, will become more apparent through reference to the following description, the accompanying drawings, and the claims. Furthermore, it is to be understood that the features of the various embodiments described herein are not mutually exclusive and may exist in various combinations and permutations. As used herein, the terms "approximately," "about," and "substantially" mean±10%. The term "consists essentially of" means excluding other materials that contribute to function, unless otherwise defined herein. Nonetheless, such other materials may be present, collectively or individually, in trace amounts.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Figure 1A:
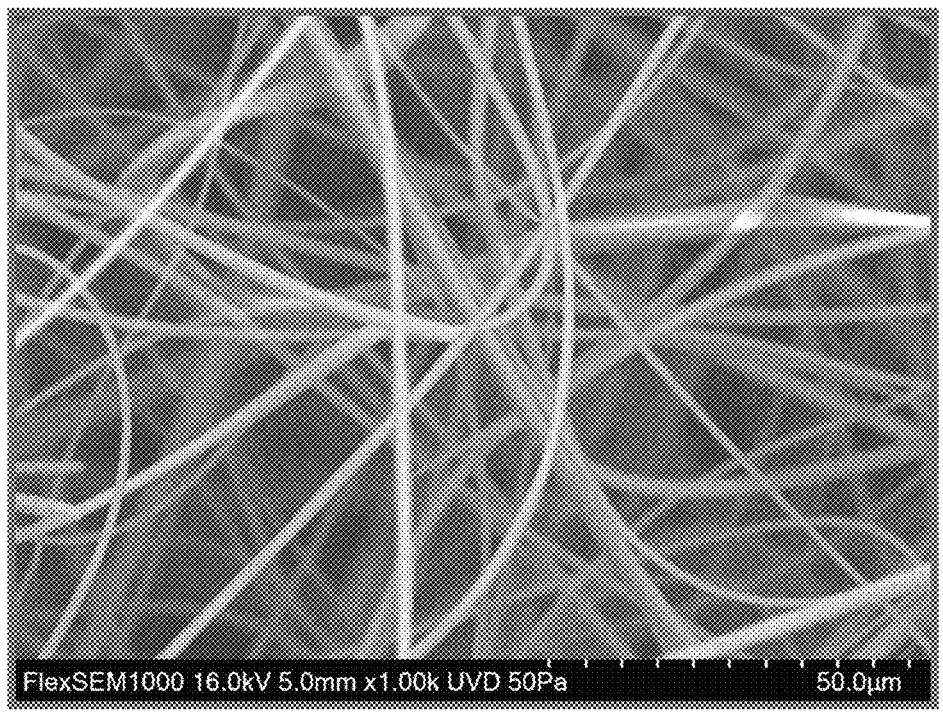
FIGS. 1A-1D are scanning electron microscopy (SEM) images of fibers spun in accordance with embodiments of the invention. Images in FIGS. 1A-1D are at, respectively, 50, 100, 200, and 500 micron scale. As shown, the fibers are flexible, smooth, dense, and continuous (not fractured).
Figure 1B:
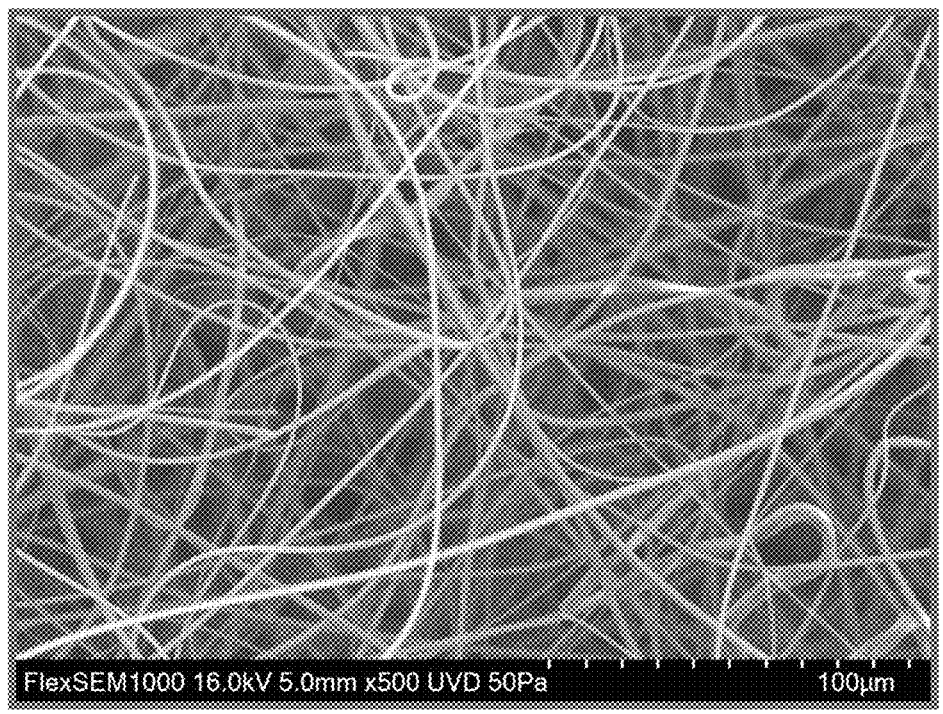
Figure 1C:
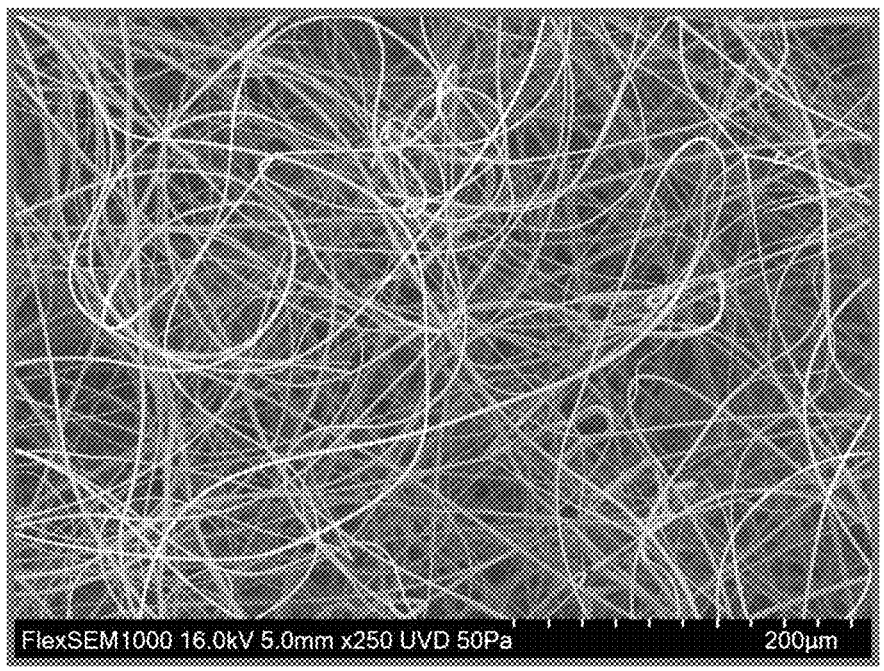
Figure 1D:
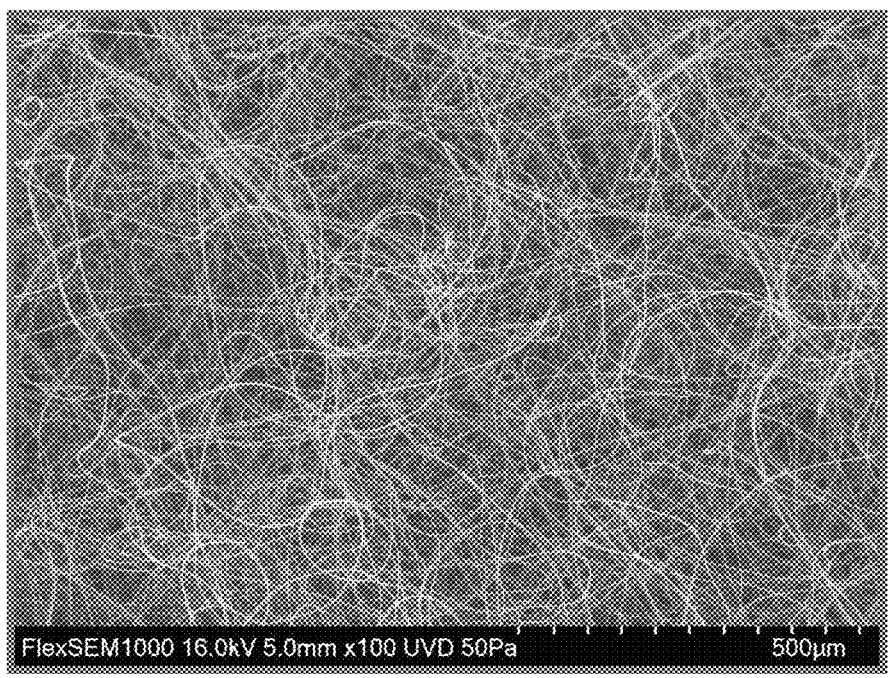

Embodiments of the present invention provide topical compositions that comprise a silica fiber powder or dust, and a topical carrier. In other aspects, the invention provides methods for treating aging or damaged skin of a subject. In various embodiments, the methods involve application of the compositions to improve skin healing, to prevent or reduce scarring, reduce signs of aging, or to reduce pain or irritation associated with damaged skin. In some embodiments, the compositions improve the look and appearance of skin.

In various embodiments, the topical composition when applied to skin allows silica fiber dust to be deposited in macroscopic or microscopic breaks in skin. The fiber dust or flakes act as a collagen mimetic that is not substantially biodegradable, and which may promote cell infiltration and/or collagen deposition, and in some embodiments reduces local production of pain and/or inflammatory mediators.

In various embodiments, the fiber dust is incorporated with a topical carrier, which may be in the form of a lotion, ointment, balm, paste, cream, foam, soap, shampoo, or gel, and may comprise other active agents.

The fiber composition is prepared by electrospinning a sol-gel into a silica fiber composition, followed by processing the fiber into a fine powder or dust, and incorporating the powder or dust with the topical carrier.

In some embodiments, the silica fiber composition is electrospun from a gelatinous material into a lightweight fiber mat. For example, the composition may be prepared by electrospinning a sol-gel, which can be prepared with a silicon alkoxide reagent, such as tetraethyl ortho silicate (TEOS), alcohol solvent, and an acid catalyst.

Known processes for electrospinning silica fibers do not yield a fiber composition with sufficient flexibility and texture suitable or ideal for topical compositions. Instead, these structures are comparatively brittle, rigid, and compact; and fiber mats are thin and will easily fracture. Generally, these materials lack the physical characteristics to mimic collagen deposition. In various embodiments, to achieve a superior material for tissue repair, it is important to electrospin the sol-gel once it is appropriately ripened, to achieve a composition with the desired physical characteristics. By slowly ripening the sol-gel under controlled environmental conditions, and/or monitoring the sol-gel during the ripening process, the relatively short window to successfully electrospin the sol-gel can be identified and increased in duration. In accordance with embodiments of the invention, the composition is non-rigid and has a soft texture similar to that of cotton.

In accordance with embodiments of the invention, the silica fiber composition, when applied to wounded tissue, acts as a non-biodegradable scaffold that supports tissue healing, regeneration, and/or integrity. The composition acts as a collagen biomimetic at the site of damaged tissue, providing an environment conducive for regeneration and growth of dermal cells and/or natural deposition of collagen. Without wishing to be bound by theory, the composition and methods described herein limit pain and inflammation at the site of damaged tissue. Further, uncontrolled tissue degradation processes can destroy newly deposited collagen. The composition of the invention provides a non-biodegradable scaffold that is not destroyed by proteases released at the site of tissue injury, but provides an optimal environment for population and growth of dermal cells. The fibers will become an integral part of the regenerating tissue.

The fibers may have a variable or more uniform diameter, such as in the range of from about 50 nm to 5 μm. In some embodiments, the fibers are predominately in the range of about 100 nm to about 2 μm, or predominately in the range of about 200 to about 1000 nm. The size(s) of the fibers is a better mimic for natural collagen, compared to, for example, brittle scaffolding including those intended to have a more uniform structure.

In some embodiments, the sol-gel for preparing the silica fiber composition is prepared by a method that includes preparing a first mixture containing an alcohol solvent, a silicon alkoxide reagent such as tetraethylorthosilicate (TEOS); preparing a second mixture containing an alcohol solvent, water, and an acid catalyst; fully titrating the second mixture into the first mixture; and processing (ripening) the combined mixture to form a gel for electrospinning. In some embodiments, the silicon alkoxide reagent is TEOS. Alternative silicon alkoxide reagents include those with the formula $Si(OR)_4$, where R is from 1 to 6, and preferably 1, 2, or 3.

In some embodiments, the sol comprises, consists essentially of, or consists of about 70% to about 90% by weight silicon alkoxide (e.g., TEOS), about 5% to about 25% by weight alcohol solvent (e.g., anhydrous ethanol), an acid catalyst (e.g., less than about 0.1% by weight when using HCl) and water. Any sol or sol-gel described herein may include the balance water (i.e., water may constitute any amount of the sol or sol-gel that is otherwise unspecified). Any sol or sol-gel described herein may optionally contain one or more reagents that may or do alter one or more properties of the sol, the sol-gel, and/or the silica fibers. Such reagents may include, but are not limited to, for example, polymers and polymeric solutions, inert reagents, alcohols, organic and/or aqueous solvents, organic salts, inorganic salts, metals, metal oxides, metal nitrides, metal oxynitrides, carbon (e.g., graphene, graphite, fullerenes, etc.), etc.

In some embodiments, the sol contains 70% to 90% tetraethyl orthosilicate (TEOS) by weight, 8% to 25% ethanol by weight, 1% to 10% water by weight, and an acid catalyst. In some embodiments, the sol contains 75% to 85% by weight TEOS, 12% to 20% by weight ethanol, and about 2% to 5% by weight water. An exemplary sol contains about 80% by weight TEOS, about 17% by weight ethanol, and about 3% by weight water. In some embodiments, the acid catalyst is HCl. For example, the sol may contain less than about 0.1% HCl by weight. For example, the sol may contain from 0.02% to 0.08% HCl by weight. In various embodiments, the sol does not contain an organic polymer, or other substantial reagents, such that the fiber composition will be substantially pure $SiO_2$. In various embodiments, the sol does not include inorganic salts (e.g., sodium chloride, lithium chloride, potassium chloride, magnesium chloride, calcium chloride, and/or barium chloride), nor are, in various embodiments, inorganic salts mixed with other components of the sol or into the sol itself. In various embodiments, the fiber composition does not include metals or metal oxides (e.g., $TiO_2$ or $ZrO_2$). In various embodiments, the fiber composition consists essentially of $SiO_2$, i.e., contains only $SiO_2$ and unintentional impurities, and, in some embodiments, species and/or complexes resulting from the incomplete conversion of the sol to $SiO_2$ (e.g., water and/or chemical groups such as ethoxy groups, silanol groups, hydroxyl groups, etc.).

In some embodiments, the alcohol solvent is an anhydrous denatured ethanol, or in some embodiments, methanol, propanol, butanol or any other suitable alcohol solvent. The first mixture may be agitated, for example, using a magnetic stirrer, vibration platform or table, or other agitation means. The second mixture contains an alcohol solvent, water, and an acid catalyst. The alcohol solvent may be an anhydrous denatured alcohol, or may be methanol, propanol, butanol or any other suitably provided alcohol solvent. Water may be distilled water or deionized water. Enough acid catalyst is added to the mixture to aid in the reaction.

This acid catalyst may be hydrochloric acid, or may be sulfuric acid or other suitable acid catalyst. The second mixture may be agitated, for example, magnetic stirrer, vibration platform or table, or other agitation means. In some embodiments, the first mixture (or sol) and the second mixture (or sol) are created without the use of direct heat (i.e., heat applied via extrinsic means such as a hot plate or other heat source).

According to various embodiments, the first mixture and the second mixture are combined by dripping or titrating the second mixture into the first mixture, preferably with agitation. The combined mixture is then further processed by allowing the sol to ripen in a controlled environment until a substantial portion of the alcohol solvent has evaporated to create a sol-gel suitable for electrospinning. For example, the controlled environment may include an enclosure with at least one vent and optionally a fan to draw gases away from the mixture, and which may involve controlled conditions in terms of humidity, temperature, and optionally barometric pressure. For example, the humidity may be controlled (e.g., via use of conventional humidifiers and/or dehumidifiers) within the range of about 30% to about 90%, such as from about 40% to about 80%, or in some embodiments, from about 50% to about 80%, or from about 50% to about 70% (e.g., about 55%, or about 60%, or about 65%). Some humidity may be helpful to slow evaporation of solvent, and thereby lengthen the window for successful electrospinning. In some embodiments, the temperature is in the range of from about 50° F. to about 90° F., such as from about 60° F. to about 80° F., or from about 65° F. to about 75° F. In various embodiments, the sol is not exposed to heat over 150° F. or heat over 100° F., so as to avoid accelerating the transition. In some embodiments, barometric pressure is optionally controlled (e.g., using a low pressure vacuum source such as a pump or a fan). By controlling the environmental conditions during ripening, the time period during which the gel may be electrospun may be lengthened; this time period may be a small window of only several minutes if the ripening process is too accelerated, such as with direct heat. When ripening the sol at a constant humidity of about 55% and temperature of about 72° F., the sol will ripen (gelatinize) in a few days, and the window for successful electrospinning may be expanded to at least several hours, and in some embodiments several days. In various embodiments, the ripening process takes at least 2 days, or at least 3 days in some embodiments. However, in various embodiments the ripening does not take more than 10 days, or more than 7 days. In some embodiments, the ripening process takes from 2 to 10 days, or from 2 to 7 days, or from 2 to 5 days, or from 2 to 4 days (e.g., about 2, about 3, or about 4 days). In various embodiments, the sol-gel is spinnable well before it transitions into a more solidified, non-flowable mass.

The enclosure space for ripening the sol-gel may include a vent on at least one surface for exhausting gases from within the enclosure, and optionally the vent may include a fan for exhausting gases produced during the ripening process. The enclosure space may optionally include a heating source (e.g., one or more heating elements, for example resistive heating elements) for providing a nominal amount of heat within the enclosure space, to maintain a preferred temperature. In some embodiments, a source of humidity (e.g., an open container of water or other aqueous, water-based liquid) is provided within the enclosure environment to adjust the humidity to a desired range or value. The enclosure may further include one or more environmental monitors, such as a temperature reading device (e.g., a thermometer, thermocouple, or other temperature sensor) and/or a humidity reading device (e.g., a hygrometer or other humidity sensor).

In some embodiments, the sol-gel is electrospun after a ripening process of at least 2 days, or at least 36 hours, or at least 3 days, or at least 4 days, or at least 5 days at the controlled environmental conditions (but in various embodiments, not more than 10 days or not more than 7 days under the controlled environmental conditions). By slowing the ripening process, the ideal time to spin the fibers can be identified. The weight of the sol-gel may be used as an indicator of when the sol-gel is at or near the ideal time to electrospin. Without intending to be bound by theory, it is believed that the viscosity of the sol-gel is a poor determinant for identifying the optimal time for electrospinning. For example, in various embodiments, the sol-gel is from about 10% to about 60% of the original weight of the sol (based on loss of alcohol solvent during transitioning). In some embodiments, the sol-gel is from 15 to 50% of the original weight of the sol, or in the range of about 20 to about 40% of the original weight of the sol.

In some embodiments, the sol-gel is ripened for at least 2 days, or at least 36 hours, or at least 3 days, or at least 4 days, or at least 5 days, and is electrospun when the ethylene vapors produced by the composition are between about 10% and about 40% of the vapors produced by the starting sol, such as in the range of about 10% and about 25%, or in the range of about 10% to about 20%. Ethylene is a colorless flammable gas with a faint sweet and musky odor (which is clearly evident as solvent evaporation slows). Ethylene is produced by the reaction of ethanol and acid. Ethylene may optionally be monitored in the vapors using a conventional ethylene monitor. In other embodiments, gases produced by the sol during the sol ripening process are monitored to determine a suitable or optimal time for electrospinning. Gas profiles may be monitored using gas chromatography.

In various embodiments, the sol-gel may be ripened for a shorter period of time, as long as the sol-gel remains spinnable via electrospinning. The resulting silica fiber mat or collection of fibers may in some cases be more brittle after ripening for a shorter time period, but such brittleness may not prevent the fragmenting of the fibers and dispersion into various different topical compositions.

The processing of the sol-gel mixture may require stirring or other agitation of the mixtures at various intervals or continuously due to the development of silicone dioxide crystalline material on the top surface of the mixtures. This development of crystalline material on the top surface slows the processing time and it is believed that the crystalline material seals off exposure of the mixture to the gaseous vacuum provided within the enclosure space. In some embodiments, any solid crystalline material is removed from the mixture.

Upon completion of the sol-gel process, the sol-gel is then electrospun using any known technique. The sol or sol-gel may be preserved (e.g., frozen or refrigerated) if needed (and such time generally will not apply to the time for ripening). An exemplary process for electrospinning the sol-gel is described in Choi, Sung-Seen, et al., *Silica nanofibers from electrospinning/sol-gel process, Journal of Materials Science Letters* 22, 2003, 891-893, which is hereby incorporated by reference in its entirety. Exemplary processes for electrospinning are further disclosed in U.S. Pat. No. 8,088,965, which is hereby incorporated by reference in its entirety.

In an exemplary electrospinning technique, the sol-gel is placed into one or more syringe pumps that are fluidly coupled to one or more spinnerets. The spinnerets are connected to a high-voltage (e.g., 5 kV to 50 kV) source and are external to and face toward a grounded collector drum. The drum rotates during spinning, typically along an axis of rotation approximately perpendicular to the spinning direction extending from the spinnerets to the drum. As the sol-gel is supplied to the spinnerets from the syringe pumps (or other holding tank), the high voltage between the spinnerets and the drum forms charged liquid jets that are deposited on the drum as small entangled fibers. As the drum rotates and electrospinning continues, a fibrous mat of silica fibers is formed around the circumference of the drum. In various embodiments, the spinnerets and syringe pump(s) may be disposed on a movable platform that is movable parallel to the length of the drum. In this manner, the length along the drum of the resulting fiber mat may be increased without increasing the number of spinnerets. The diameter of the drum may also be increased to increase the areal size of the electrospun mat. The thickness of the mat may be largely dependent upon the amount of sol-gel used for spinning and thus the amount of electrospinning time. For example, the mat may have a thickness of greater than about ⅛ inch, or greater than about ¼ inch, or greater than about ⅓ inch, or greater than about ½ inch.

After completion of the electrospinning process, the resulting mat is removed from the drum. For example, the mat may be cut and peeled away from the drum in one or more pieces. The mat may then be divided into small fibrous fragments that may be incorporated into the topical composition. In various embodiments, the resulting fibrous fragments are each intertwined collections of silica fibers, rather than unitary solid particles. In some embodiments, the electrospun mat may be fractured, cut, ground, milled, or otherwise divided into small fragments that maintain a fibrous structure. In some embodiments, the mat (or one or more portions thereof) is rubbed through one or more screens or sieves, and the mesh size of the screen determines, at least in part, the size of the resulting fibrous fragments or powder or dust produced from the electrospun mat. For example, the mat or mat portions may be rubbed through a succession of two or more screens having decreasing mesh sizes (e.g., screens having mesh numbers of 100, 200, 300, or even 400), in order to produce a powder or dust or collection of fibrous fragments having the desired sizes.

The fiber dust or fibrous fragments are incorporated with a topical carrier, which can be in the form of a lotion, ointment, balm, paste, cream, foam, soap, shampoo, conditioner, or gel. The topical composition can be a skin care composition or a cosmetic composition. In some embodiments, the fiber dust or fragments are distributed in a carrier system such as water or any aqueous solution containing organic or inorganic materials. The compositions may contain one or more ingredients to modify or enhance their texture, appearance, scent performance or stability. Illustrative additives to the compositions include: oily components, fatty components, ointment bases, hydrophilic solvents, lipophilic solvents, emollients, water, buffering agents, pH-adjusting agents, preservatives, humectants, chelating agents, antioxidants, stabilizers, emulsifying agents, detergents, suspending agents, gel-forming agents, perfumes and fragrances, skin protective agents, and antiseptics.

In various embodiments, the fiber dust or fibrous fragments are incorporated into the composition at from about 5 mg/ml to about 500 mg/ml, or from about 5 mg/ml to about 400 mg/ml, or from about 5 mg/ml to about 250 mg/ml. In some embodiments, the dust or fiber fragments are incorporated into the composition at from about 10 mg/ml to about 200 mg/ml, or from about 10 mg/ml to about 150 mg/ml, or from about 25 mg/ml to about 100 mg/ml.

The topical composition may comprise oily or fatty components, which are constituents of the hydrophobic phase, and can include one or more of: almond oil, castor oil, cacao butter, coconut oil, corn oil, cottonseed oil, linseed oil, olive oil, palm oil, peanut oil, poppy seed oil, rapeseed oil, sesame oil, soybean oil, sunflower oil, teaseed oil, jojoba oil, mineral oils, silicone oils, fatty oils, liquid paraffin, beeswax, lanolin, white soft paraffin, yellow soft paraffin, petrolatum, triglycerides, cetyl alcohol, stearyl alcohol, isopropyl myristate, oleic acid, isopropyl palmitate, stearic acid, sorbitan esters of fatty acids, sorbitan esters of fatty acids and ethylene oxide (including Tween).

The topical composition may comprise an aqueous phase, which constitutes the hydrophilic phase and which may comprise water, one or more other hydrophilic solvents, and/or one or more surfactants and/or emulsifier. In various embodiments, the aqueous phase may comprise solvents such as water, polyethylene glycol, propylene glycol, glycerol, sorbitol, and alcohols such as ethanol and isopropyl alcohol.

The composition may comprise one or more emulsifiers (emulsifying agents), which can be part of the aqueous phase and/or oil phase. The term "emulsifier" means an amphiphilic molecule possessing both polar and non-polar regions which are covalently bound and capable of reducing the surface tension of water and for the interfacial tension between water and an immiscible liquid. Emulsifiers include soaps, detergents, surface active agents, and the like. The emulsifier can be cationic, anionic, non-ionic, or amphoteric. Exemplary emulsifiers include non-ionic emulsifiers such as polyol esters (e.g. ethylene glycol, diethylene glycol, glycol stearate and propylene glycol monoesters of fatty acids), and glycerol esters (e.g. glyceryl stearate, glyceryl monooleate, glycerylmonolaurate, glyceryl ricinolate, glyceryl monocaprylate). Exemplary emulsifiers further include Sorbitan derivatives, which are esters of cyclic anhydrides of sorbitol with a fatty acid. These include sorbitan monolaurate, sorbitan monooleate, sorbitan monostearate, sorbitan monopalmitate, sorbitan sesquioleate, sorbitan trioleate, sorbitan tristearate, polyoxyethylene sorbitan esters (e.g. polyoxyethylene sorbitan monostearate, polyoxyethylene sorbitan tristearate, polyoxyethylene sorbitan monooleate). Exemplary emulsifiers also include polyoxyethylene esters, which are mixtures of mono- or di-fatty acids esters (from C12 to C18) of polyoxyethylene glycol. These include stearate esters of PEG (PEG-40, PEG-50 and PEG-55), as well as laurate, oleate, and myristate esters of PEG.

The composition can comprise polymeric thickeners including gums such as acacia, alginates, carageenan, chitosan, collagen, tragacanth and xantham; celluloses, acrylic acids, colloidal solids such as silica, clays and microcrystalline cellulose, hydrogels such as polyvinyl alcohol and polyvinylpyrrolidone, as well as thermoreversible polymers such as poloxamers.

The composition may further comprise one or more pharmaceutical or antimicrobial agents suitable for topical application. Exemplary pharmaceutical agents include antifibrotic and anti-scarring agents.

In some embodiments, the composition comprises an antibiotic or antiseptic. Antibiotics suitable for use in the present invention include, but are not limited to, cephalosporin antibiotics, tetracycline antibiotics, beta-lactams, carbapenem antibiotics, polymyxin B (neosporin), neomycin, and bacitracin. Antiseptics include, without limitation, phenol, meta-cresol, methylparaben, and sodium benzoate.

In some embodiments, the composition further comprises one or more anti-inflammatory agents such as steroidal anti-inflammatory agents or non-steroidal anti-inflammatory agents (NSAIDs). Steroids, particularly the adrenal corticosteroids and their synthetic analogues, are well known in the art. Examples of corticosteroids include, without limitation, hydroxyltriamcinolone, alpha-methyl dexamethasone, beta-methyl betamethasone, beclomethasone dipropionate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, triamcinolone acetonide, cortisone, cortodoxone, flucetonide, fludrocortisone, difluorosone diacetate, fluradrenolone acetonide, medrysone, amcinafel, amcinafide, betamethasone, chloroprednisone, clocortelone, clescinolone, dichlorisone, difluprednate, flucloronide, flunisolide, fluoromethalone, fluperolone, fluprednisolone, hydrocortisone, paramethasone, prednisolone, methylprednisolone, prednisone, and budesonide. NSAIDS that may be used in the composition, include salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In some embodiments, the composition comprises at least one active agent for reducing pain, including but not limited to cortisone, hydrocortisone, acetaminophen, or a cannabinoid.

In various embodiments, the invention provides a method for treating skin tissue in a subject. The method comprises applying the topical composition described herein to skin tissue. The composition can be applied routinely or periodically. In some embodiments, the composition is applied at least about daily, and in some embodiments from 1 to about 10 times per day. In various embodiments, the method improves healing of the skin tissue and/or prevents or reduces tissue scarring, looseness of skin, signs of aging, pain, and/or irritation.

Application of the composition can provide for improved or accelerated healing of damaged skin. For example, when the topical composition is applied to skin that has cracks, small scrapes, blemishes, etc., the scaffolding is left behind in the small "wound" for cells to grow into. This speeds up the healing process and helps to reduce scarring. In some embodiments, the composition in lotion or other form is applied to the cracked skin (e.g., on the face, mouth or lips, neck, hands, arms, shoulders, legs, scalp, fingers, etc.) to improve tolerance of the skin to the environment, such as sun, wind, and cold, thereby reducing the impact of age and environment on the appearance, feel, and/or function of the skin. In some embodiments, the composition is a lip balm, which can comprise the silica dust suspended in a wax base (e.g., carnauba wax, paraffin, and/or beeswax). Alternatively, the lip balm may be an ointment, e.g., comprising petroleum jelly or similar base, including bases described herein. In still other embodiments, the composition is applied as a soap or shampoo during bathing. In some embodiments, the silica composition is a bath salt employed for bathing.

In some embodiments, the composition is applied to an insect or spider bite or sting, including bee sting, wasp sting, mosquito bite, spider bite, flea bite, fly or ant bites, bits from bed bugs, or others. In some embodiments, the composition is applied to skin that has been contacted with or is manifesting a reaction to poison ivy or poison oak. In other embodiments, the composition is applied to a skin allergic reaction or hives. The composition in these embodiments may include additional agents to reduce itch or swelling (e.g., corticosteroid or antihistamine), pain (e.g., acetaminophen or NSAID), or allergic responses (e.g., antihistamine). Exemplary antihistamines include brompheniramine, carbinoxamine maleate, chlorpheniramine, clemastine, diphenhydramine, hydroxyzine triprolidine, cetirizine, desloratadine, fexofenadine, levocetirizine, loratadine, and oloptadine.

In some embodiments, the composition is applied to skin showing signs of microbial infection, including HPV (e.g., wart), herpes simplex virus (e.g., cold sore), varicella-zoster virus (e.g., chicken pox or shingles), fungal infection (e.g., candidiasis or tinea versicolor), or *staphylococcus* infection or over colonization. In some embodiments, the composition comprises one or more antibiotics (e.g., antibacterial or anti-fungal agent), antiviral agent, or antiseptic.

In some embodiments, the subject is a mammal. Subjects include veterinary patients such as a dog, cat, or horse, among others. In some embodiments, the patient is a human patient. In some embodiments, the patient is a pediatric patient.

In some embodiments, the composition is applied to a skin lesion, superficial wound or infection (e.g., acne), burn, cut, scrape, rash (e.g., diaper rash), blister (including ruptured blister), or hives. In some embodiments, the composition is applied to cracked or scraped skin. In some embodiments, the composition is applied to aging skin or dry skin, including eczema, atopic dermatitis, or pruritus. In some embodiments, the topical composition normalizes the tissue microenvironment, and may reduce pain and inflammation at the site, and/or provide a microscaffold for dermal cells to multiply and grow into, and in some embodiments induce collagen deposition. In some embodiments, the subject has a first, second, or third degree burn, or a combination thereof. In some embodiments, the composition is applied to a sun burn, and reduces pain or discomfort. In some embodiments, the composition is applied to a post-surgery wound, including skin graft, skin comprising sutures, or cosmetic surgery wound.

For treatment of severe wounds and burns, it may first be necessary to apply portions of fiber mats directly to the wound for several days (see U.S. Pat. No. 10,111,783, which is hereby incorporated by reference in its entirety). For example, in some embodiments, a portion of a fiber mat is applied to the tissue or wound as a thin layer of fibers, e.g., just enough to cover the wound surface. Often, the wound will quickly absorb the fibers. The process is repeated once fibers are no longer visible on the wound. For example, in some embodiments, fibers are reapplied 2 to 5 times per day. Once new skin is substantially formed over the wound or burn area, the subject transitions to application of the lotion described herein. Lotion is general applied one or more time daily, and can be used continuously until the skin barrier has normalized.

In some embodiments, the composition is applied to age spots (e.g., solar lentigines). Applying the composition routinely (e.g., at least daily) for several days can fade or reduce visible age spots.

In some embodiments, because the fiber material substantially reduces pain from the site of tissue damage, the patient may be able to forgo therapy with a pain medication such as an opioid.

In some embodiments, the subject has a genetic disease that impacts skin barrier function, such as but not limited to epidermolysis bullosa or ichthyosis.

Epidermolysis bullosa (EB) is a group of mainly inherited connective tissue diseases that cause blisters in the skin and mucosal membranes. It is a result of a defect in anchoring between the epidermis and dermis, resulting in friction and skin fragility. EB often involves formation of blisters following trivial trauma.

In some embodiments, the subject has epidermolysis bullosa simplex, which results in blisters at the site of rubbing, and typically affects the hands and feet. In some embodiments, the subject has junctional epidermolysis bullosa, which affects laminin and collagen. Junctional epidermolysis bullosa also presents with blisters at the site of friction, especially on the hands and feet. Dystrophic epidermolysis bullosa is an inherited variant affecting the skin and other organs, and involves skin that is very fragile. Dystrophic epidermolysis bullosa is caused by genetic defects (or mutations) within the gene encoding the protein type VII collagen (collagen VII).

The human skin consists of two layers: an outermost layer called the epidermis and a layer underneath called the dermis. In individuals with healthy skin, there are protein anchors between these two layers that prevent them from moving independently from one another (shearing). In people born with EB, the two skin layers lack the protein anchors that hold them together, resulting in extremely fragile skin. Even minor mechanical friction (like rubbing or pressure) or trauma will separate the layers of the skin and form blisters and painful sores. Sufferers of EB have compared the sores with third-degree burns.

In some embodiments, the subject has ichthyosis. Ichthyosis is a family of genetic skin disorders characterized by dry, thickened, scaly skin. The more than 20 types of ichthyosis range in severity of symptoms, outward appearance, and underlying genetic cause. The severity of symptoms can vary, from the mildest, most common, types such as ichthyosis vulgaris, which may be mistaken for normal dry skin, up to life-threatening conditions such as harlequin-type ichthyosis. In various embodiments, the topical composition is applied to a subject having any of the types of ichthyosis, including harlequin ichthyosis.

In some embodiments, the composition is applied to diseased skin, which can be a manifestation of a proliferative disorder (e.g., carcinoma, pre-carcinoma, or melanoma lesion, or other cancer lesion, or psoriasis), or in some embodiments an autoimmune or inflammatory disorder. For example, in some embodiments, the composition is applied for treatment of rosacea or acne. Autoimmune manifestations include cutaneous manifestation of lupus and dermatitis herpetiformis, or dermatomyositis. In some embodiments, the composition is applied to skin affected by shingles, providing, for example, relief from associated pain and reduction in associated rash. In some embodiments, including but not limited to subjects experiencing shingles, psoriasis, or eczema, the composition can be applied topically to affected areas of the skin, or alternatively, applied during bathing (using a soap, shampoo, or bath salt composition comprising the silica dust).

Other conditions that benefit from the composition in some embodiments include neuropathy, joint pain, and gout. In some embodiments, the composition is applied to the skin in the area of the pain (for example, to generally intact skin surrounding a painful joint).

In some embodiments, the composition is applied to the affected area at least about daily for at least about 1 week, or at least about 2 weeks. In some embodiments, the composition is applied between once and ten times per day, or in some embodiments, from once to about four times per day, or from one to three times daily. In some embodiments, the regimen is continued for at least one week, or at least two weeks, or at least one month, or at least two months, or at least four months, or at least six months, or more. In some embodiments, the regimen is continued for six months or more. For subjects having a genetic disease of the skin, the regimen may be continuous.

Embodiments of the invention will now be described with respect to the following examples.

EXAMPLES

Example 1: Preparation of Silica Fiber Mat

Silica fibers were prepared using an electrospinning process, in which a sol-gel was spun onto a collector drum to form a non-woven mat of fibers. The sol-gel was made in two parts. First, TEOS was mixed with ethanol, and then a second mixture containing HCl, water, and ethanol was titrated into the mixture. The sol-gel was then allowed to ripen for a few days under controlled conditions before spinning.

In one example, the first sol was made by weighing out 384 grams of TEOS 98% and 41.8 grams of anhydrous denatured ethanol, and pouring together. The first sol was allowed to let stand in a beaker, and a magnetic stirrer was used to create a homogenous solution. The second sol was made by weighing 41.8 grams of anhydrous denatured ethanol, 16.4 grams of distilled water, and 0.34 grams of hydrochloric acid, which was then poured together and mixed for 8 seconds with a magnetic stirrer until a homogenous second sol was formed.

The second sol was then poured into the titration device, which was placed above a beaker containing the first sol. The titration device then dripped about 5 drops per second until a third sol was formed via the mixing of the first sol and the second sol. During the dripping process, the first sol was continuously mixed with a magnetic stirrer while the second sol was dripped into the first sol.

The combined third sol was then placed into an enclosure box. A low pressure vacuum was provided by a fan on medium speed to remove fumes. The air temperature within the box was 72° F. with 60% humidity. The third sol was allowed to sit and process for about three days. The mixtures were agitated daily to reduce the build-up of crystalline structures. The third sol began to transition to sol-gel with evaporation of the alcohol solvent. Sol-gel may be monitored to determine an approximate amount of $C_2H_4$ (ethylene) in the vapors, which may be in the range of about 10-20% relative to that of the original sol before ripening. Upon proper gelatinization, the sol-gel was loaded into electrospinning machine or was frozen to preserve for electrospinning. In this example, proper gelatinization occurred when the total mass of the sol-gel was between about 70 grams and about 140 grams. This example may be scaled appropriately and the ranges may vary, yet still produce desirable structures. To further identify the ideal time to electropsin, portions of the gel may be dripped into the electric field of the spinning apparatus to evaluate the spinning properties of the sol-gel.

Figure 2:
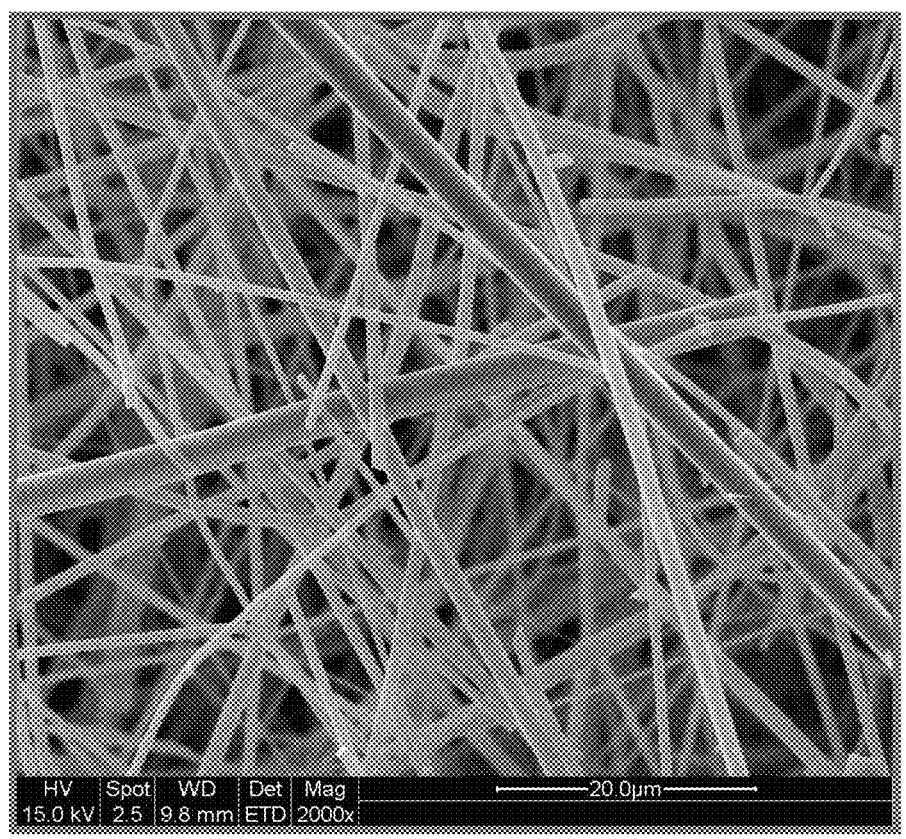
FIG. 2 shows an SEM image (20 micron scale is shown) of fibers spun at a non-optimal time. The fibers are rigid, with fractures clearly evident.
Figure 3:
FIG. 3 shows a fiber mat spun with a thickness of about ¼ inch in accordance with embodiments of the invention. The mat has a soft, flexible texture.

FIGS. 1A-1D are scanning electron microscopy (SEM) images of fibers spun in accordance with embodiments of the invention (50, 100, 200, and 500 micron scales shown). As shown, the fibers are flexible, smooth, dense, and continuous (not significantly fractured). FIG. 2 is an SEM image of fibers that were electrospun at a non-optimal time (before the sol-gel was fully ripened) (20 micron scale shown), where the fibers are clearly rigid with many fractures clearly evident. FIG. 3 shows a fiber mat spun in accordance with embodiments of the invention. The flexibility and continuity of the fibers allows mats to be spun at a thickness of ¼ inch or more. The mat has a soft, flexible texture.

Figure 4A:
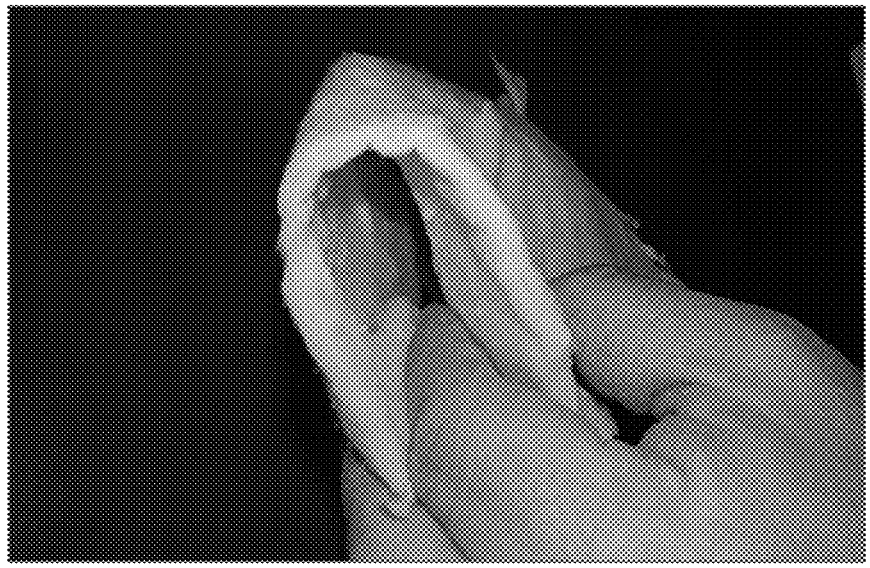
FIGS. 4A and 4B compare a silica fiber mat that was electrospun when the sol-gel was transitioned in accordance with certain embodiments of the invention (FIG. 4A), with a fiber mat that was spun early, before the sol-gel was optimally ripened (FIG. 4B).
Figure 4B:

FIGS. 4A and 4B are images comparing a silica fiber mat that was electrospun when the sol-gel was ripened in accordance with embodiments of the invention (FIG. 4A), with a fiber mat that was spun too early, before the sol-gel was optimally ripened or ripened too fast (FIG. 4B). The material in FIG. 4A has a soft texture, is very flexible, and can be spun at a thickness that is easily processed into dust-like particles. The material in FIG. 4B is brittle, inflexible, and thin.

Figure 5A:
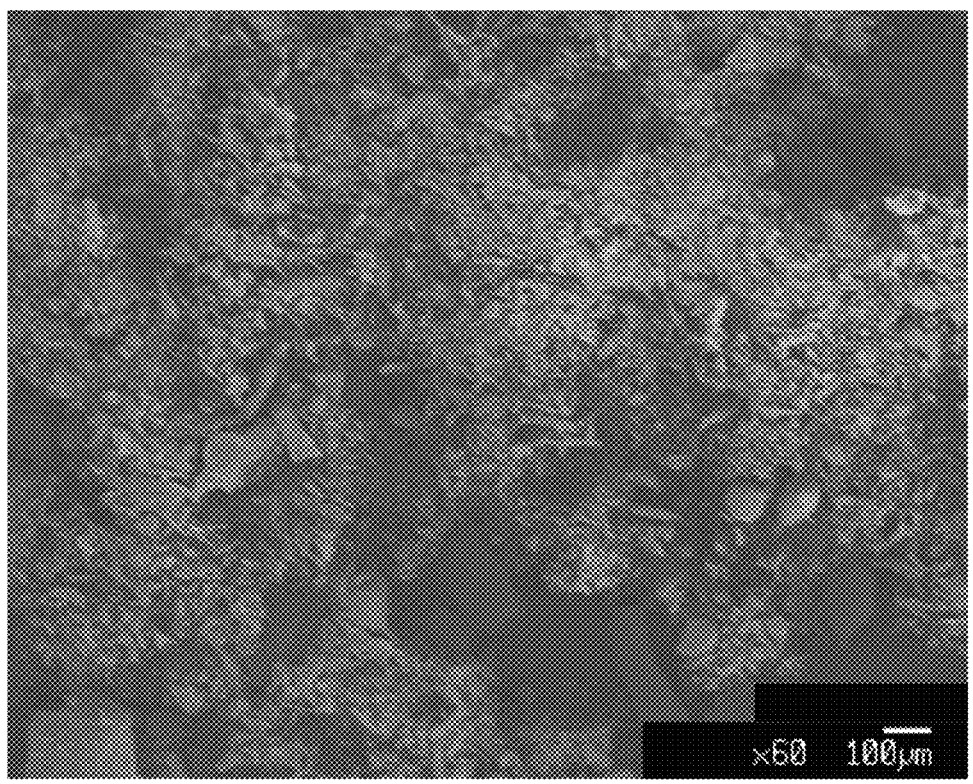
FIGS. 5A and 5B show SEM images of fiber dust in accordance with embodiments of the invention, with 100 μm scale shown.
Figure 5B:
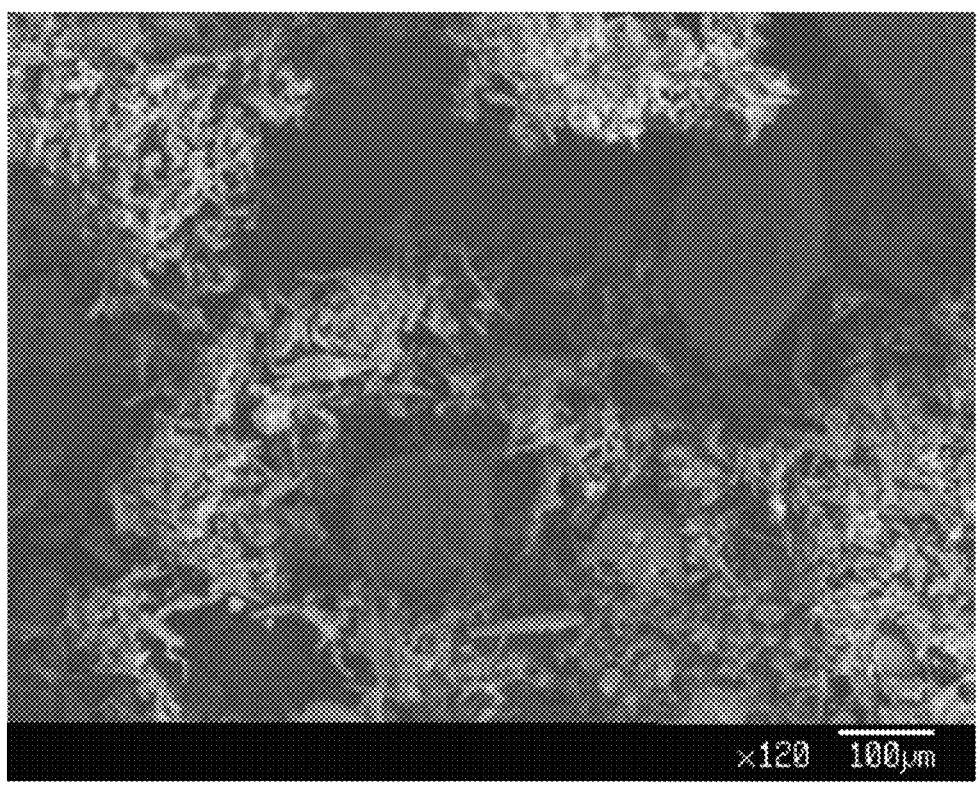

A silica fiber mat was fabricated and broken into fragments by rubbing through a series of screens of decreasing mesh size. The final screen was a 200 mesh screen, resulting in fiber dust and/or fibrous fragments having sizes of approximately 20 µm to approximately 200 µm. FIGS. 5A and 5B show SEM images of the resulting fiber dust, with 100 µm scale shown. The soft texture of the material remains evident in the dust form.

For incorporating into a topical composition, a silica fiber mat prepared as described above was rubbed through a 100 mesh screen. The resulting silica fiber dust was incorporated into different topical compositions including: petroleum jelly, bacitracin ointment, facial cream, hand cream, and acne cream.

Example 2: Treatment of Shingles

A paste was prepared with bacitracin ointment and silica fiber dust. The paste was applied to the skin of a middle-age woman experiencing shingles. The ointment relieved the pain associated with the shingles. Petroleum jelly-silica fiber composition was also applied to affected areas with similar results.

Figure 6A:
FIGS. 6A and 6B show a shingles rash prior to treatment with a silica fiber topical composition in accordance with embodiments of the invention (FIG. 6A) and the rash after of about 1.5 days with frequent application in accordance with embodiments of the invention (FIG. 6B).
Figure 6B:

An exemplary treatment of shingles is shown in FIGS. 6A and 6B. FIG. 6A shows the initial shingles rash, and FIG. 6B shows the same rash after about 1.5 days, with the topical composition being applied. Pain was also substantially reduced. Typically, it takes several weeks for a shingles rash to resolve.

Example 3: Treatment of Age Spots

A silica fiber composition prepared with generic facial cream was prepared as described. The composition was applied over the course of 10 days to age spots on the face of an adult male. Over 10 days the spots were substantially faded.

Example 4: Treatment of Scar Tissue

A silica fiber composition was prepared with generic hand cream. The composition was used routinely by an adult woman with scarring and dermatitis marks on her hands. Over time, the scarring and dermatitis marks subsided.

Example 5: Treatment of Acne

A silica fiber composition was prepared with acne cream, and applied to the face of a female with acne blemishes and acne scarring on her face. With routine application, the scars and blemishes subsided.

Example 6: Burn Treatment

Figure 7A:
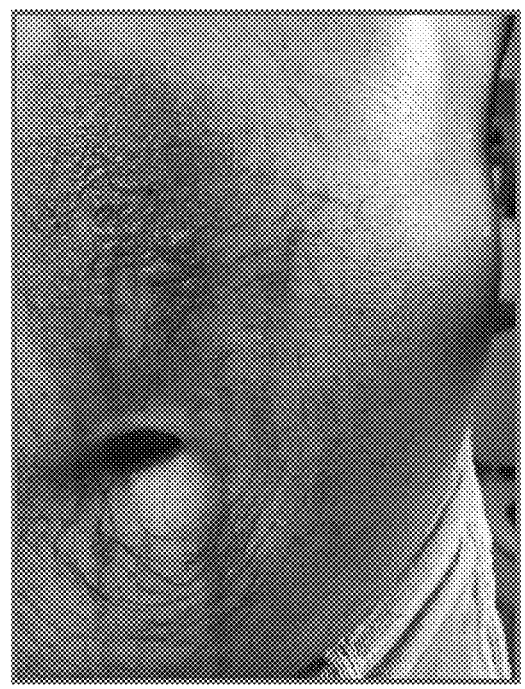
FIG. 7A shows a burn prior to treatment with a silica fiber topical composition in accordance with embodiments of the invention.
Figure 7B:
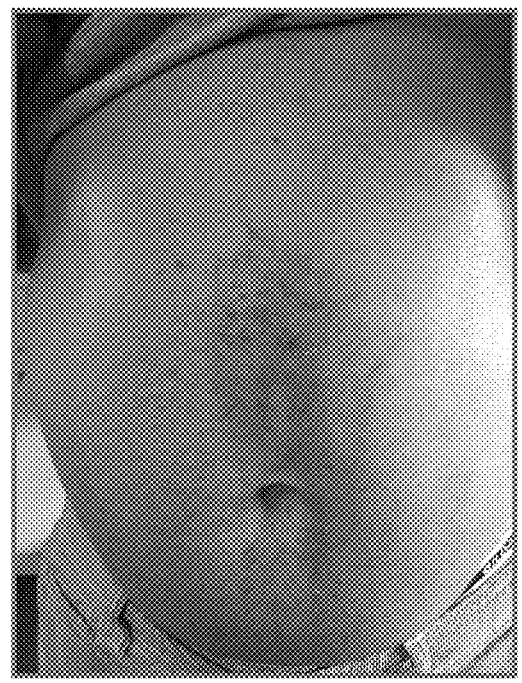
FIG. 7B shows the burn of FIG. 7A after of about 4 days of frequent application with a silica fiber topical composition in accordance with embodiments of the invention.

A silica fiber composition was applied to the torso of a middle-aged male having a first/second degree burn. With routine application, the burn was substantially healed in about 4 days (compare FIG. 7A with FIG. 7B).

In another example, a middle-aged male suffered 2nd and 3rd degree burns resulting from an explosion. The burns covered the right hand and much of the right arm, extending from the fingers to above the elbow. After about one week from the accident, treatment with the silica fibers was initiated. The subject was still experiencing a significant amount of pain prior to treatment. Within minutes of application of the fibers to the wound, the pain was reported to be substantially alleviated. Sensations of tightness were reported.

Once the fibers were removed by showering, the pain returned, though were lessened. With further application of the fibers, the pain was again substantially alleviated. By the following day, silica matrix would not simply wash from the wound by showering. For the next week, the burns were dressed with the fiber matrix 2 to 3 times per day. By day 3, the skin had started to grow back. After a little over one week, the majority of the skin had grown back over the wound area.

Once the new skin was formed over the burned area, treatment transitioned to a lotion with the silica matrix. The lotion was applied to the burned area two to four times daily as necessary. After a couple weeks of using the lotion, there was no visible scarring from the burns. There is slight discoloration in the pigment of the skin, which fades over time.

Example 7: Treatment of Ichthyosis

A lotion composition was applied to the skin of a female subject (about 18 months of age) having harlequin Ichthyosis. It was observed that the rate at which excess skin was being produced had slowed drastically. Is was further observed that the subject's body was better hydrated, most likely because the skin production was slower, and the extremely high caloric needs were drastically reduced.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

The invention claimed is:

1. A method for treating a wound or burn in a subject, the method comprising:
   applying a first portion of silica fiber mat directly to damaged skin tissue of said wound or burn as a thin fiber layer sufficient to cover a surface of the wound or burn, and applying one or more additional first portions of silica fiber mat when fibers are no longer visible on the surface of the wound or burn, wherein tithe silica fiber mat is prepared by producing a sol-gel from a sol and electrospinning the sol-gel into the silica fiber mat, and (ii) said first portions of silica fiber mat are not processed into powder or dust prior to application to the damaged skin tissue; and
   after formation of new skin over the damaged skin tissue, applying a topical composition to said new skin, the topical composition comprising (i) a silica fiber powder or dust at an amount that is from 10 mg/mL to 200 mg/mL, and (ii) a topical lotion, wherein the composition is prepared by processing a second portion of silica fiber mat into powder or dust and incorporating the powder or dust with the topical lotion, the silica fiber powder or dust providing a porous fibrous scaffold supporting cell infiltration.

2. The method of claim 1, wherein the method improves healing of the damaged skin tissue and/or reduces tissue scarring, pain, and/or irritation.

3. The method of claim 1, wherein the subject is a mammal.

4. The method of claim 3, wherein the subject is a veterinary patient selected from the group consisting of a dog, cat, or horse.

5. The method of claim 3, wherein the subject is a human patient.

6. The method of claim 1, wherein the subject has a genetic disease that impacts skin integrity.

7. The method of claim 6, wherein the subject has epidermolysis bullosa or ichthyosis.

8. The method of claim 1, wherein the subject has a first, second, and/or third degree burns.

9. The method of claim 1, wherein the composition further comprises one or more pharmaceutical or antimicrobial agents.

10. The method of claim 1, wherein the composition further comprises an antibiotic, an antiseptic, an anti-inflammatory agent, an immunosuppressant, a pain reducing agent, an anti-fibrotic, or an anti-scarring agent.

11. The method of claim 1, wherein the sol comprises 70% to 90% tetraethyl orthosilicate (TEOS) by weight, 8% to 25% ethanol by weight, an acid catalyst, and water.

12. The method of claim 11, wherein the sol is allowed to ripen for at least 2 days with humidity controlled within the range of about 40% to about 80%, and the temperature controlled within the range of 50 to 90° F.

13. The method of claim 12, wherein the sol is allowed to ripen for 2 to 7 days.

14. The method of claim 1, wherein the second portion of silica fiber mat is processed into powder or dust via rubbing the second portion of silica fiber mat through a succession of two or more screens or sieves having decreasing mesh sizes.

15. The method of claim 1, wherein the silica fiber powder or dust comprises intertwined collections of silica fibers having sharp and/or broken edges.

16. The method of claim 1, wherein the average size of fibrous fragments of the silica powder or dust is in the range of 20 μm to 200 μm.

17. The method of claim 1, wherein the composition is applied to the new skin at least twice daily.

18. The method of claim 17, wherein the composition is applied to the new skin from 2 to 10 times per day.

19. The method of claim 1, wherein the second portion of silica fiber mat is processed into powder or dust via rubbing the second portion of silica fiber mat through one or more screens or sieves.

20. The method of claim 1, wherein applying one or more additional first portions of silica fiber mat when fibers are no longer visible on the surface of the wound or burn comprises applying a plurality of first portions of silica fiber mat to said damaged skin tissue at least daily, for multiple days.

21. The method of claim 1, wherein:
the silica fiber powder or dust comprises fibrous fragments each comprising an intertwined collection of silica fibers having sharp and/or broken edges; and
the average size of the fibrous fragments is in the range of 20 μm to 200 μm.

\* \* \* \* \*